(12) United States Patent
Rodriguez et al.

(10) Patent No.: US 6,541,673 B1
(45) Date of Patent: Apr. 1, 2003

(54) PROCESS FOR OXYALKYLATING PHENOLIC COMPOUNDS

(75) Inventors: Carmen L. Rodriguez, Gulph Mills, PA (US); Jude T. Ruszkay, Coatesville, PA (US)

(73) Assignee: ARCO Chemical Technology, L.P., Greenville, DE (US)

( * ) Notice: Subject to any disclaimer, the term of this patent is extended or adjusted under 35 U.S.C. 154(b) by 40 days.

(21) Appl. No.: 09/997,887

(22) Filed: Nov. 30, 2001

(51) Int. Cl.$^7$ ............................................... C07C 41/03
(52) U.S. Cl. ..................... 568/633; 568/631; 568/640; 568/643; 568/646; 568/650; 568/651; 568/652; 568/654
(58) Field of Search ................................. 568/631, 633, 568/640, 643, 646, 650, 651, 652, 654

(56) References Cited

U.S. PATENT DOCUMENTS

| | | | | |
|---|---|---|---|---|
| 2,782,240 A | * | 2/1957 | Hefner et al. ............... | 568/608 |
| 3,803,246 A | * | 4/1974 | Rosnezweig et al. ........ | 528/219 |
| 4,167,538 A | | 9/1979 | Taniguchi et al. .......... | 525/438 |
| 4,241,201 A | | 12/1980 | Annis ......................... | 525/503 |
| 5,158,922 A | | 10/1992 | Hinney et al. ............... | 502/175 |
| 5,470,813 A | | 11/1995 | Le-Khac ..................... | 502/175 |
| 5,482,908 A | * | 1/1996 | Le-Khac ..................... | 502/156 |
| 5,545,601 A | | 8/1996 | Le-Khac ..................... | 502/156 |
| 5,639,705 A | | 6/1997 | Bowman et al. ............. | 502/175 |
| 5,889,137 A | | 3/1999 | Hutchings et al. .......... | 528/205 |
| 6,245,877 B1 | | 6/2001 | Rodriguez et al. ............ | 528/79 |

FOREIGN PATENT DOCUMENTS

| WO | WO 97/19972 | 6/1997 |
|---|---|---|

\* cited by examiner

*Primary Examiner*—Rosalynd Keys
(74) *Attorney, Agent, or Firm*—Brooks & Kushman P.C.

(57) ABSTRACT

Phenolic polyether polyols are prepared by a two stage oxyalkylation process, a first stage performed at a high oxyalkylation temperature and a second stage at a lower oxyalkylation temperature. Despite the use of high temperature during oxyalkylation, polydispersity is substantially unaffected, while process time is drastically reduced.

20 Claims, 1 Drawing Sheet

PROCESS FOR OXYALKYLATING PHENOLIC COMPOUNDS

BACKGROUND OF THE INVENTION

1. Field of the Invention

The present invention pertains to aryl polyols prepared by oxyalkylating starter molecules containing phenolic hydroxyl groups, and to the aryl polyols obtained thereby.

2. Background Art

Oxyalkylation of hydroxyl-functional starter molecules to prepare hydroxyalkyl-terminated polyols, generally hydroxyalkyl-terminated polyether polyols, has been practiced for some time. The physicochemical properties of the polyols are tailored to the particular end use. In general, low viscosities, relatively low polydispersity, and relatively low color are required of these products. In order that the polyols may be provided cost effectively, the production process is preferably of short duration.

Preparation of phenolic-based polyols is more problematic than those prepared from starters bearing aliphatic hydroxyl groups. The decreased basicity of alkali metal phenoxides and related compounds lowers the oxyalkylation rate considerably. In addition to the slow oxyalkylation, phenolic starters exhibit a relatively long "induction time" prior to attaining a reasonable oxyalkylation rate.

Moreover, unlike the oxyalkylation of starters such as ethylene glycol, trimethylolpropane, and the like, where a homogenous or substantially homogenous reaction mixture is obtained during alkylene oxide addition, alkylene oxides are poorly soluble in phenolic compounds and vice versa. Thus, oxyalkylation of phenolic starters must generally take place in solution. Aromatic solvents such as toluene or xylene are preferred. However, the addition of solvent lowers the reaction rate due to dilution effects, and also requires subsequent removal of solvent, adding to the already long processing time.

The requirement for low viscosity products has been thought to require that relatively low oxyalkylation temperatures should be used, i.e., in the range of 100° C. to 125° C., as are conventionally used with aliphatic glycol-based polyether polyols. Increasing the temperature generally broadens the molecular weight distribution considerably, and increases the color of the product as well.

It would be desirable to provide a process for the preparation of aryl polyols which is less time consuming, and therefore more cost-effective. It would be further desirable to lower the induction time exhibited by phenolic starters, and to minimize solvent recovery. It would be yet further desirable to provide lower viscosity polyols at a given hydroxyl content.

SUMMARY OF THE INVENTION

It has now been surprisingly discovered that significant improvements may be made in the preparation of aryl polyols by a staged temperature process wherein a first oxyalkylation is conducted at a relatively high temperature, and further oxyalkylation conducted at a lower temperature. Contrary to what would be expected, the viscosity and polydispersity of the product polyols remain substantially the same, and in some cases are lowered, while dramatically decreasing both the induction period and the overall reaction time. The products are useful for many purposes, and may be aminated by conventional amination procedures to produce aminated products.

DETAILED DESCRIPTION OF THE PREFERRED EMBODIMENTS

Figure 1:
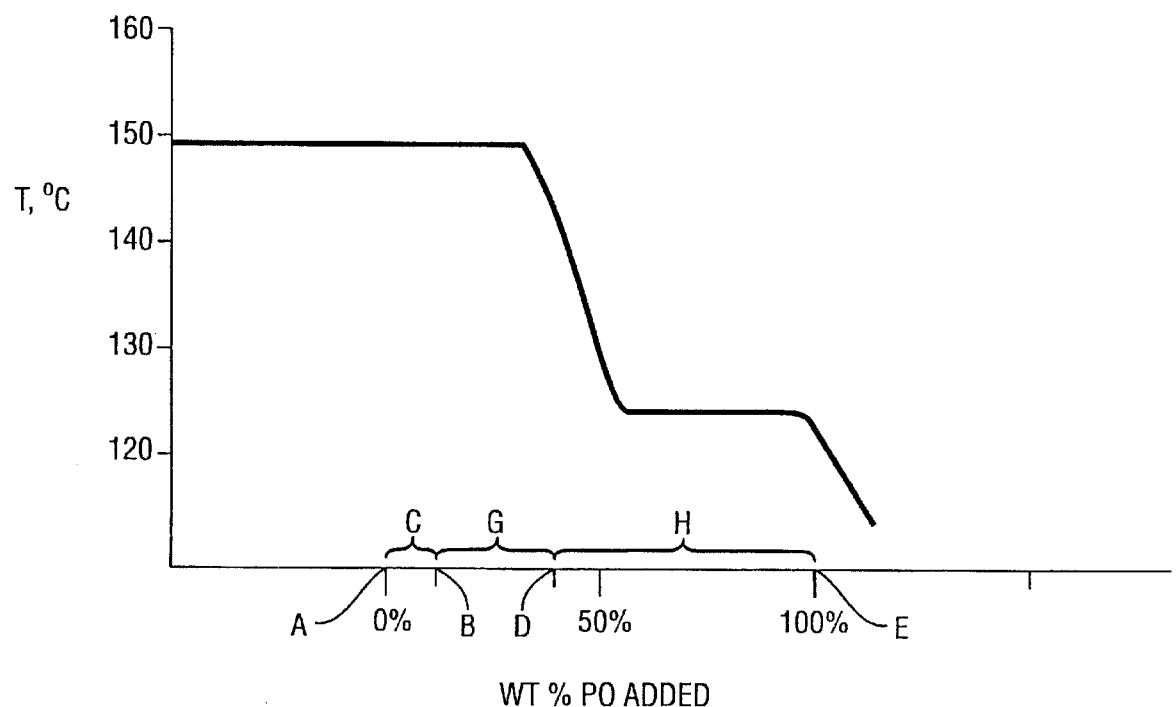
FIG. 1 illustrates schematically a plot of reaction temperature versus weight percent of alkylene oxide addition for one embodiment of the present invention.

The invention pertains to a staged process for preparation of aryl polyols where an initial portion of the oxyalkylation is conducted at a high temperature, while a second oxyalkylation is conducted at a lower temperature. Optionally, the alkylene oxide pressure is staged also, with the highest pressure occurring during the high temperature phase of the reaction. While the process is described hereafter with respect to "oxypropylation," this term is inclusive of the use of other alkylene oxides in addition to or in lieu of propylene oxide, as indicated below.

By "aryl polyol" is meant a polyol produced by oxyalkylating a phenolic starter molecule containing at least two phenolic hydroxyl groups, and preferably from 2 to 10, more preferably 2 to 8 phenolic hydroxyl groups. The phenolic starter may be a single ring compound or may be a condensed ring compound, i.e., 1,4-dihydroxynaphthalene, but is preferably a multi-ring compound such as 4,4'-dihydroxybiphenyl or bisphenol A. Most preferably, the phenolic starter is an aralkylated phenolic compound prepared by aralkylating a phenol such as bisphenol A with styrene or another aryl-substituted alkene. The aralkylated phenols may be coupled by reaction with an aldehyde such as formaldehyde, or are preferably coupled by reaction with a dialkenylaryl compound such as divinylbenzene or the like. By coupling in this fashion, phenolic starters having from 2 to 10 phenolic hydroxyl groups may be readily prepared. Preferred phenolic starters bear non-condensed aryl groups linked to phenolic hydroxyl-containing rings through alkylene linking groups. Further details of such preparations may be obtained by reference to U.S. Pat. Nos. 4,167,583; 4,241,201; 5,889,137; and 6,234,877, which are herein incorporated by reference. Preferred phenolic starters are styrenated bisphenol A, with a phenolic hydroxyl functionality of 2, and bisphenol A coupled by means of formaldehyde, with an average functionality of about 4.

The oxyalkylation takes place with alkylene oxide(s), preferably propylene oxide, optionally in admixture with less than 50 mol percent (i.e., a "minority") of ethylene oxide. The propylene oxide or propylene oxide mixture may also contain other higher alkylene oxides such as 1,2-butylene oxide, 2,3-butylene oxide, and styrene oxide. The latter alkylene oxides as well as other conventionally used alkylene oxides may be used alone as well, or in admixture with other alkylene oxides. Preferably used are propylene oxide or mixtures of propylene oxide and less than 40 mol percent ethylene oxide, more preferably less than 30 mol percent ethylene oxide, and yet more preferably less than 20 mol percent ethylene oxide. Most preferably, the alkylene oxide employed is substantially all propylene oxide, i.e. containing less than 5 mol percent of all other alkylene oxide moieties, and in particular, is all propylene oxide. By the term "oxypropylation" as used herein is meant oxyalkylation with propylene oxide alone or an alkylene oxide mixture containing a majority (>50 mol percent) of propylene oxide, unless indicated clearly to the contrary. The terms "major" and "majority" mean more than 50 percent on a mol or weight basis as the case may be.

The oxyalkylation is performed at two different temperatures, a first temperature which is significantly higher than normal oxyalkylation temperatures, i.e., higher than 135° C., more preferably higher than 140° C., preferably in the range of 140–160° C., most preferably 145–155° C. The upper limit is dictated predominately by the thermal stability of the starter and the necessity to avoid highly colored products. This upper temperature will vary dependent upon the starter molecule, but is generally below 180° C., most often below 170° C., and is preferably no higher than 160–165° C.

The first, high temperature oxyalkylation preferably takes place at the outset of the reaction, i.e., the reactor is heated to the desired temperature prior to introduction of alkylene oxide into the reactor. Under these conditions, induction time and overall cycle time are minimized to the maximum extent. However, it would not depart from the spirit of the invention to first add alkylene oxide at a lower temperature, i.e., 100–125° C., and then ramp the temperature to the desired high temperature, or even to maintain the reactor below 135° C. for a short length of time prior to heating to the higher temperature. In any case, to achieve the desired results, at least 20 percent of the total oxyalkylation as hereinafter defined, should occur at the higher temperature, and at least 20 percent of the total low temperature oxyalkylation should occur following the high temperature phase.

By the term "total oxyalkylation" is meant the period following the induction period at which oxyalkylation occurs at a reasonable rate, and extending to the end of alkylene oxide addition.

By the term "low temperature oxyalkylation" is meant the period following the end of high temperature oxyalkylation until the end of oxyalkylation, i.e., to the end of alkylene oxide addition prior to the cookout or stripping phase. These periods may be more fully described later with reference to FIGS. 1 and 2.

By "induction period" is meant the time following introduction of alkylene oxide, and in the presence of catalyst, when the oxyalkylation rate remains low, as indicated by no substantial decline in pressure. The induction period is over when an observable, significant pressure drop occurs. The term "induction period" is well known to those skilled in the art of oxyalkylation with alkylene oxides.

Figure 2:
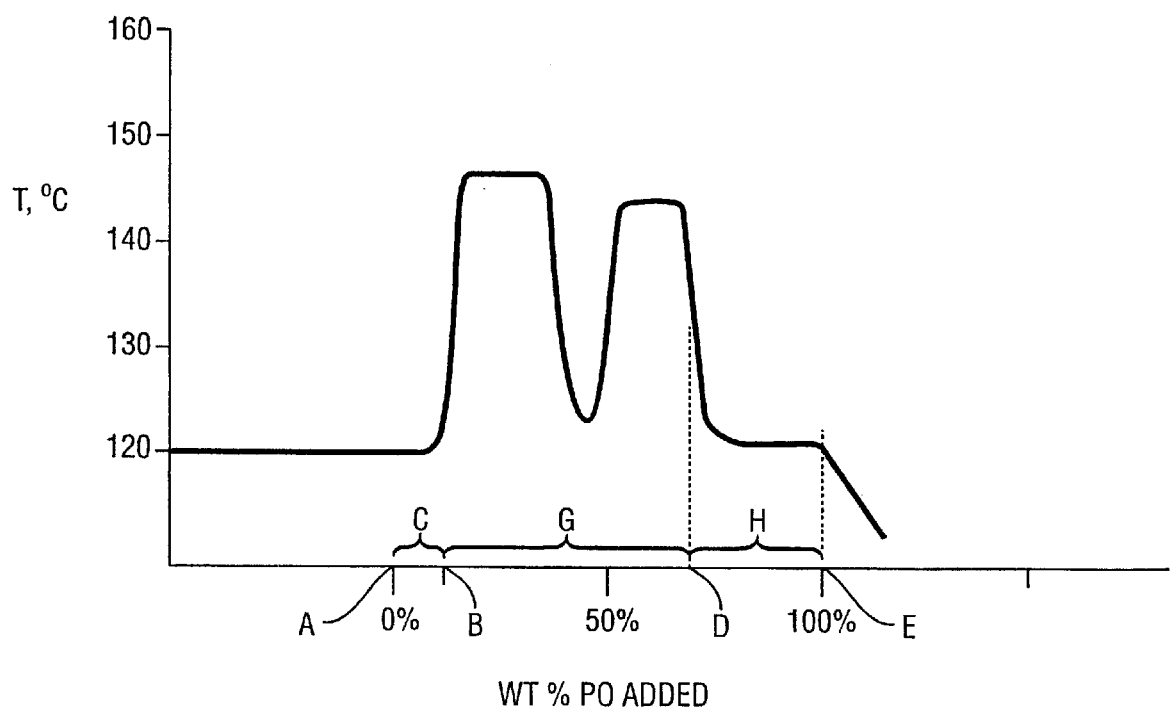
FIG. 2 illustrates schematically a plot of reaction temperature versus weight percent of alkylene oxide addition for a second embodiment of the present invention.

FIG. 1 illustrates a plot of temperature against wt. % propylene oxide ("PO") for a typical reaction within the scope of the invention, with significant events noted. The reactor, containing phenolic starter, solvent, and catalyst is heated to 150° C. and propylene oxide feed started at A. The propylene oxide pressure observably declines at B, signifying the end of the induction period C. At D, the reactor temperature is lowered, signifying the end of the high temperature oxypropylation period G and the beginning of low temperature oxypropylation. Propylene oxide feed is ceased at E, and the propylene oxide pressure then drops during cookout. The low temperature reaction time is period H, between points D and E. FIG. 2 shows a less preferred temperature/wt. % PO curve where the high temperature reaction is delayed, and also the high temperature oxyalkylation period is interrupted by a low temperature addition. The letters A through H have the same meaning as in FIG. 1.

In the present process, it is preferred that the high temperature oxypropylation period (G in FIGS. 1 and 2) be at least 20 percent of the total oxyalkylation period (G+H), more preferably at least 30 percent, and yet more preferably in the range of 40 to 60 percent, most preferably about 50 percent. If the high temperature period is extended significantly past 60 percent, the polydispersity may increase and the product color may deepen as well. If the high temperature oxypropylation is less than 20 percent of the total oxypropylation period, the processing time will increase and more solvent may be required, and the amount of unsaturated product obtained may be affected. Note that these periods, although categorized herein as time periods, are actually based on alkylene oxide added. They may, for any given system, be easily converted to time periods per se.

The catalysts employed are those conventionally employed in oxyalkylation. Tertiary amine catalysts, alkali metal basic catalysts such as alkali metal hydroxides or alkoxides, and double metal cyanide complex catalysts may all be used, as well as useful combinations, i.e., combinations of tertiary amine and alkali metal hydroxides. Double metal cyanide complex catalysts, for example (but not by limitation) those disclosed in U.S. Pat. Nos. 5,158,922; 5,639,705; 5,470,813; 5,545,601; and 5,482,908 are particularly useful in certain instances, since these catalysts may, in preferred embodiments, be used in concentrations low enough that they may be left in the product, or removed by simple filtration. Thus, use of these catalysts can avoid polyol product treatment with magnesium silicate and subsequent rather slow filtration of the resulting slurry, as well as disposal of the filter cake which is ordinarily used to remove basic catalyst residues. As a result, the process is more economical both in terms of process time as well as economy of raw materials usage. However, in general, double metal cyanide complex catalysts must be employed in larger amounts than when oxyalkylating aliphatic hydroxyl-containing compounds such as alcohols, glycols, triols, and the like. Preferably, from 50 ppm to 1000 ppm of double metal cyanide complex catalysts are used, more preferably 100 ppm to 700 ppm, and most preferably 150 ppm to 350 ppm, the concentration in parts per million (ppm) based on final product weight.

A solvent is generally necessary. In conventional oxyalkylation of phenolic starters, it has been usual to employ approximately the same amount of solvent as phenolic starter, or more than this amount, on a weight/weight basis. This amount of solvent is the amount necessary to fully dissolve the phenolic starter at room temperature. Thus, at the end of alkylene oxide addition, products having hydroxyl numbers in the range of 50 to 200 may have as much as 30 percent residual solvent in the final product, which must be removed by vacuum distillation, stripping, etc., to relatively low levels. It has surprisingly been found that the initial amount of solvent may easily be reduced to half the normal amount or even 30 percent of this amount or less without causing processing difficulties. As a result, the solvent content of the product is much reduced, and stripping time is reduced considerably as well. It has been surprisingly discovered that when double metal cyanide complex catalysts are used, solvents may be entirely dispensed with, yet oxyalkylation occurs at acceptable rates and generates products of good color. In such processes, it is desirable to employ a substantial amount of the heel of a prior batch.

The preferred solvent is toluene, although other hydrocarbon solvents such as n-hexane, n-heptane, cyclopentane, cyclohexane, xylene, ethylbenzene, etc. may be used. Aromatic solvents such as toluene and xylene (single isomer or mixture of isomers) are preferred. Commercial aromatic solvents which are more complex mixtures of aryl compounds are also acceptable. Also suitable, but less preferred, are ether-type solvents such as tetrahydrofuran and dioxane, and aprotic polar solvents. such as dimethylformamide, dimethylsulfoxide, dimethylacetamide, and the like.

The products are useful in a variety of ways, including use as polyols in the preparation of polyurethanes and polyureas. In addition, the products may be derivatized to form amines, acrylates, polyacids, and esters, and the like. When aminated by conventional methods, they produce amino-functional products useful, inter alia, as hardeners for epoxy resins, chain extenders for polyurethane resins, as intermediates for the preparation of polyureas and other derivatives, and as crosslinkers and fuel additives. The products may also serve as reactive diluents, flexibilizers, and intermediates in formulations where these are commonly used. These uses are merely illustrative, and not limiting.

The following examples merely illustrate the present invention. Those skilled in the art will recognize many variations that are within the spirit of the invention and scope of the claims. In the Examples and Comparative Examples which follow, the di-functional phenolic starter and hexa-functional starter are prepared in accordance with starter preparations as described in WO97/19972.

COMPARATIVE EXAMPLE C1
Conventional Oxyalkylation

To 579.6 g toluene is added 495.4 g difunctional phenolic starter and 3.24 g potassium hydroxide oxyalkylation catalyst. The solution is refluxed and dried to less than 0.02 weight percent water. The solution is transferred to a stainless steel pressure reactor and flushed with nitrogen. After heating to conventional oxyalkylation temperature, 125° C., propylene oxide is added to 20 psig (95 g). The mixture is monitored to determine initiation of oxyalkylation, which occurs after an induction period of 2 hours 8 minutes, as evidenced by an observable pressure drop of about 2 psi. Propylene oxide is then added initially at 20 psig and maintained below 50 psig until a polyol of the desired molecular weight is obtained. Propylene addition time is about 10 hours. Reaction parameters are summarized in Table 1 below, and product properties in Table 2.

COMPARATIVE EXAMPLE C2
Oxyalkylation with Reduced Solvent and Increased Catalyst Comparative Example C1 is repeated, but with an unconventional amount of solvent in an attempt to decrease overall process time. The amount of solvent is cut in half. The induction period decreases to 24 minutes and the overall reaction time is reduced to about seven hours.

EXAMPLE 3
(Subject Invention)

The process of Comparative Example C1 is followed, but with only half the amount of toluene solvent, as in Comparative Example C2. However, the reaction is brought to 150° C. prior to propylene oxide addition and maintained at that point until approximately one-half of total propylene oxide addition. The reactor temperature is then lowered to 130° C. for the remainder of propylene oxide addition. The induction period is only 5 minutes. Reaction parameters and product properties are reported in Tables 1 and 2, respectively.

COMPARATIVE EXAMPLE 4

The process of Comparative Example C1 is followed, employing conventional amounts of solvent and oxyalkylating at conventional temperature, but with 0.5 weight percent KOH catalyst, and employing a hexafunctional phenolic starter rather than a difunctional starter. The initiation time is 40 minutes and propylene oxide addition time 342 minutes, for a total cycle time of 382 minutes, about 6 and one third hours. The reaction parameters are summarized in Table 1 and product properties in Table 2.

EXAMPLE 5
(Subject Invention)

The same starter and catalyst amount employed in Comparative Example C4 are employed with reduced solvent, one third the amount used in Comparative Example C4, and a staged temperature profile, the initial oxyalkylation temperature being 150° C., followed by a lower temperature of 135° C. The initiation period is only 10 minutes, and total propylene oxide addition time is reduced to 114 minutes. Notably, the unsaturation is decidedly less than that obtained in Comparison Example C4 indicating less monofunctional oxypropylated allylalcohol species derived from propylene oxide rearrangement, despite the higher reaction temperature. Polydispersity was also lower. The reaction parameters and product properties are reported in Tables 1 and 2 respectively.

TABLE 1

| Example | KOH Level % wt[1] | Solvent (Relative to C1) | Temp (° C.) | Init. Time (minutes) | PO Addn. Time (minutes) | Total Rxn Time (minutes) |
|---|---|---|---|---|---|---|
| Comparative Example C1 | 0.25 | 1 | 125 | 128 | 600 | 728 |
| Comparative Example C2 | 0.25 | 0.5 | 125 | 73 | 364 | 436 |
| Example 3 | 0.25 | 0.5 | 150/130 | 5 | 120 | 125 |
| Comparative Example C4 | 0.50 | 1 | 125 | 40 | 342 | 382 |
| Example 5 | 0.50 | 0.33 | 150/130 | 10 | 114 | 124 |

[1]weight percent based on product weight

Table 1 illustrates the dramatic effect of employing a higher initial reaction temperature on the initiation, propylene oxide addition time, and total process time. These highly improved results are accomplished with relatively small amounts of solvent, in contrast to the usual amounts (Comparative Example C1 ) which are used in phenolic polyol oxyalkylation. Comparative Example C2 illustrates that the improvement in process time cannot be attributed to reduced solvent alone. Even with reduced solvent, without the two stage reaction of the present invention, process time was still approximately 7 hours.

TABLE 2

| | Hydroxyl Number (mg KOH/g) | Viscosity (cps) | Mn | Mw | Mw/Mn | Unsaturation (meq KOH/g) |
|---|---|---|---|---|---|---|
| Comparative Example C1 | 82.6 | 4015 | 812 | 960 | 1.18 | 0.08 |
| Comparative Example C2 | 85 | 5228 | 824 | 991 | 1.20 | 0.07 |
| Example 3 | 72.0 | 5570 | 938 | 1119 | 1.23 | 0.09 |
| Comparative Example C4 | 62.6 | 3812 | 1961 | 4763 | 2.43 | 0.11 |
| Example 5 | 67.7 | 4884 | 1939 | 4017 | 2.07 | 0.06 |

Table 2 presents further surprising results. The viscosity of polyols produced by the subject invention process are not increased as compared to polyols prepared using only a single, conventional oxyalkylation temperature. The Example 3 polyol exhibits only a slightly higher viscosity than the Comparative Example C2 polyol, produced at the same solvent content. However, the average molecular weight of the Example 3 polyol is considerably higher than that of the C2 polyol (about 20% higher). In the case of hexafunctional starters, a slight increase in viscosity is also observed. However, this increase is believed due to the lower amount of oligomeric monofunctional species, as indicated by the considerably lower unsaturation. This decrease in unsaturation is unexpected since higher temperatures are believed to increase the rate of propylene oxide rearrangement to allyl alcohol. Even more surprising is that the polydispersity of the product polyols is similar to or in the case of the hexaftinctional polyols, considerably lower than the polydispersity obtained at lower oxyalkylation temperatures. It is well known that oxyalkylation at higher temperatures generally increases polydispersity significantly. The products of the subject invention process are obtained with a commercially highly significant decrease in overall reaction time, about only 20 percent of the reaction time of the conventional process (Comparative Example C1). Moreover, only a relatively small amount of solvent need be removed from the product, further shortening the overall process time. The improvements are obtained even without increasing catalyst levels.

EXAMPLE 6 AND COMPARATIVE EXAMPLE C7

Two solventless oxypropylations are performed on difunctional phenolic starters employing 250 ppm of double metal cyanide complex catalyst at a temperature of 130° C. (Comparative Example C7) and a staged temperature of 140° C./130° C. (Example 6). In each case, the starter and catalyst are introduced into the reactor in the presence of about 50 weight percent of the heel of a prior batch, stripped with nitrogen, and 5% of the total propylene oxide charge added initially. The pressure is observed until a noticeable pressure drop occurred, indicating activation of the double metal cyanide complex catalyst. The feed of the remaining propylene oxide is then commenced. Following cessation of the propylene oxide feed, the product is "soaked" for 30 minutes and stripped of unreacted propylene oxide for 30 minutes at full vacuum. The reactor is then cooled and the product discharged. The reaction parameters and product properties are summarized in Table 3.

TABLE 3

| | Reaction Temp | | | | | |
| --- | --- | --- | --- | --- | --- | --- |
| Example | 1st Half | 2nd Half | Catalyst Level | Solvent | OH# | Viscosity |
| Example 6 | 140° C. | 130° C. | 250 ppm | none | 92 | 2600 cps |
| Comparative Example C7 | 130° C. | 130° C. | 250 ppm | none | 89 | 4300 cps |

Preparation of polyoxyalkylated phenolic starters without employing solvent is not practiced commercially, regardless of temperature. The staged temperature process surprisingly produces a product of much lower viscosity.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for the reduction of cycle time in the preparation of oxyalkylated phenolic polyols, said process comprising:
   a) providing a phenolic starter compound having from 2 to 10 phenolic hydroxyl groups in a reactor;
   b) optionally adding a portion of hydrocarbon solvent in which said phenolic starter is soluble;
   c) adding an oxyalkylation catalyst;
   d) oxyalkylating said phenolic starter with alkylene oxide (s) at a first temperature above 135° C. until at least 20 mol percent of total alkylene oxide has been added to said reactor;
   e) further oxyalkylating at a second temperature below 135° C., said first temperature and said second temperature differing by at least 10° C., wherein at least 20 mol percent of total oxyalkylation takes place at said second temperature below 135° C.; and
   f) removing hydrocarbon solvent if present.

2. The process of claim 1 wherein said first temperature is minimally 140° C. and said second temperature is maximally 130° C.

3. The process of claim 1 wherein said alkylene oxide(s) comprise greater than 50 mol percent propylene oxide based on total alkylene oxide.

4. The process of claim 1 wherein said hydrocarbon solvent is present in less than an amount required to dissolve said phenolic starter.

5. The process of claim 4 wherein the amount of hydrocarbon solvent is 50 weight percent or less of the weight of said phenolic starter.

6. The process of claim 1 wherein the total alkylene oxide addition time is less than 40 percent of the alkylene oxide addition period for a reaction of similar stoichiometry and hydrocarbon solvent content, but performed at a single oxyalkylation temperature of 125° C.

7. The process of claim 1 wherein the propylene oxide pressure during at least a portion of step d) is higher than the average propylene oxide pressure of step e).

8. The process of claim 1 wherein said phenolic starter comprises an aralkylated phenolic starter.

9. The process of claim 1 wherein said phenolic starter comprises an aralkylated phenolic compound having one or more phenolic hydroxyl groups and coupled by means of an aldehyde or a bis(aliphatically unsaturated) aryl compound to form a phenolic starter having on average minimally two phenolic hydroxyl groups.

10. The process of claim 9 wherein said phenolic starter has on average from 2 to 8 phenolic hydroxyl groups.

11. The process of claim 1 wherein said oxyalkylating is performed with propylene oxide alone.

12. The process of claim 1 wherein the amount of hydrocarbon solvent and said first temperature are selected such that the induction period preceding significant oxyalkylation is less than 10 minutes.

13. The process of claim 1 wherein said oxyalkylation catalyst comprises an alkali metal hydroxide or alkoxide.

14. The process of claim 1 wherein said oxyalkylation catalyst comprises a double metal cyanide complex catalyst.

15. The process of claim 14, wherein substantially no organic solvent is employed.

16. The process of claim 1 wherein said hydrocarbon solvent is present in an amount of 50 percent by weight or less of the amount of hydrocarbon solvent necessary to dissolve said phenolic starter, wherein said first temperature is from 145 to 160° C., and wherein said second temperature is 130° C. or less.

17. The phenolic polyether polyol of claim 16 wherein said phenolic starter comprises an aralkylated phenolic compound having one or more phenolic hydroxyl groups and coupled by means of an aldehyde or a bis (aliphatically unsaturated)aryl compound to form a phenolic starter having an average minimally two phenolic hydroxyl groups.

18. The process of claim 1, wherein said oxyalkylation catalyst is potassium hydroxide.

19. The process of claim 1, wherein said hydrocarbon solvent is present, and is an aromatic solvent.

20. The process of claim 19, wherein said aromatic solvent comprises toluene.

\* \* \* \* \*